(12) United States Patent
Pollyea

(10) Patent No.: US 8,956,302 B2
(45) Date of Patent: Feb. 17, 2015

(54) TRIPLE LAYER PROTECTIVE LINER FOR USE WITH BLOOD PRESSURE CUFF

(76) Inventor: Susan L. Pollyea, Los Angeles, CA (US)

(*) Notice: Subject to any disclaimer, the term of this patent is extended or adjusted under 35 U.S.C. 154(b) by 334 days.

(21) Appl. No.: 12/839,089

(22) Filed: Jul. 19, 2010

(65) Prior Publication Data

US 2012/0016248 A1    Jan. 19, 2012

(51) Int. Cl.
*A61B 5/02* (2006.01)
*A61B 5/022* (2006.01)

(52) U.S. Cl.
CPC ....... *A61B 5/02233* (2013.01); *A61B 2562/247* (2013.01)
USPC ........................................................ 600/499

(58) Field of Classification Search
CPC ... A61B 5/02233; A61F 13/04; A61K 9/7023
USPC ................... 600/479, 481, 490–499
See application file for complete search history.

(56) References Cited

U.S. PATENT DOCUMENTS

| | | | | |
|---|---|---|---|---|
| 4,235,228 A | * | 11/1980 | Gaylord et al. | 602/8 |
| 4,344,999 A | * | 8/1982 | Gohlke | 128/849 |
| 4,548,249 A | | 10/1985 | Slaughterbeck | |
| 4,671,266 A | | 6/1987 | Lengyel et al. | |
| 4,966,136 A | * | 10/1990 | Bates | 602/18 |
| 4,967,758 A | | 11/1990 | Masciarotte | |
| 5,065,600 A | | 11/1991 | Byles | |
| 5,251,646 A | | 10/1993 | Bowen | |
| 5,392,782 A | * | 2/1995 | Garrett | 600/499 |
| 5,396,894 A | | 3/1995 | Eide et al. | |
| H1585 H | | 8/1996 | Ahr | |
| 5,648,136 A | | 7/1997 | Bird | |
| 5,660,182 A | * | 8/1997 | Kuroshaki et al. | 600/499 |
| 5,746,213 A | * | 5/1998 | Marks | 600/499 |
| 5,780,048 A | | 7/1998 | Lee | |
| 5,875,493 A | | 3/1999 | MacDonald et al. | |
| 5,891,957 A | | 4/1999 | Hansen et al. | |
| 5,908,693 A | | 6/1999 | Delgado et al. | |
| 5,938,874 A | | 8/1999 | Palomo et al. | |
| 6,040,251 A | | 3/2000 | Caldwell | |
| 6,171,985 B1 | | 1/2001 | Joseph et al. | |
| 6,210,352 B1 | | 4/2001 | Williams et al. | |
| 6,262,330 B1 | * | 7/2001 | Fujisawa et al. | 602/54 |
| 6,364,843 B1 | * | 4/2002 | Lightle | 600/490 |
| 6,368,687 B1 | | 4/2002 | Joseph et al. | |

(Continued)

OTHER PUBLICATIONS

Kahan, Ernesto et al., Comparison of Blood Pressure Measurments on the Bare Arm, Below a Rolled-Up Sleeve, or Over a Sleeve, Oxford University Press 2003, Family Practice vol. 20, No. 6, pp. 730-732.

(Continued)

*Primary Examiner* — Jacqueline Cheng
*Assistant Examiner* — Puya Agahi
(74) *Attorney, Agent, or Firm* — Fulwider Patton LLP

(57) ABSTRACT

A protective liner for use with a blood pressure measuring cuff includes three layers of material configured to protect a person's skin, wick moisture away from the person's skin, and provide a moisture permeable, microporous barrier to microbes. The protective liner is porous and sufficiently thin so that the protective liner will not substantially interfere with blood pressure monitoring through the protective liner. The three layers of material are configured to wick moisture therethrough away from the person's skin, while substantially preventing passage of microbes therethrough.

20 Claims, 4 Drawing Sheets

(56) References Cited

U.S. PATENT DOCUMENTS

| | | | |
|---|---|---|---|
| 6,479,073 | B1 | 11/2002 | Lucast et al. |
| 6,572,600 | B1* | 6/2003 | Roe et al. .................. 604/389 |
| 6,588,149 | B2 | 7/2003 | Weder |
| 7,097,040 | B1 | 8/2006 | Gutentag |
| 7,311,670 | B2 | 12/2007 | Just et al. |
| 7,517,151 | B2 | 4/2009 | Leone et al. |
| 7,626,071 | B2 | 12/2009 | Masini |
| 7,718,241 | B2 | 5/2010 | Wittmeyer, Jr. |
| 2008/0236596 | A1* | 10/2008 | Pierskalla et al. ............ 128/846 |
| 2009/0133446 | A1 | 5/2009 | Burrow et al. |
| 2010/0256717 | A1* | 10/2010 | Brown .................. 607/115 |

OTHER PUBLICATIONS

McKay, PhD, Donald, Measuring Blood Pressure: A Call to Bare Arms?, CMAJ-JAMC, Feb. 26, 2008; 178(5), pp. 591-593.

Senti, G. et al., Antimicrobial Silk Clothing in the Treatment of Atopic Dematitis Proves Comparable to Topical Corticosteroid Treatment, Dermatology, vol. 213, No. 3, 2006, pp. 228-233.

Internet Web Site:—wound.smith-nephew.com/au/node.asp?nodeid=3784, Smith&Nephew, Microporous Hypoallergenic Paper Tape, 4 Pages.

Internet Web Site:—www.tidiproducts.com/newsarticle1.html, News@TIDI, Tidi Products, LLC ("TIDI") Introduces Blood Pressure Cuff Barrier, Aug. 2008, 1 Page.

* cited by examiner

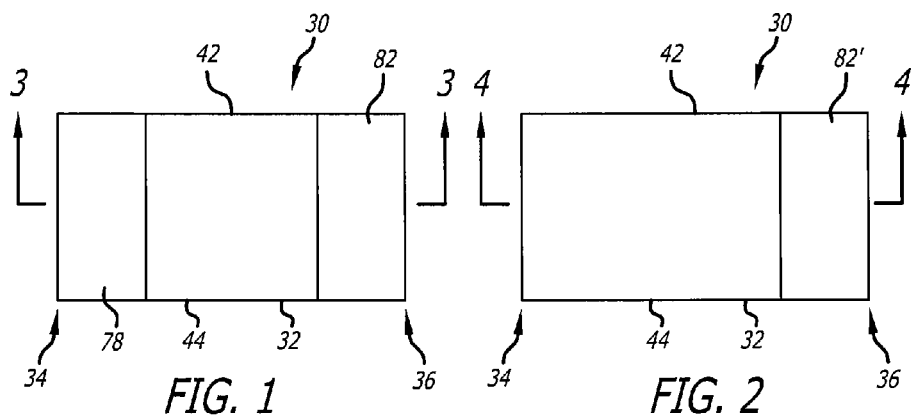
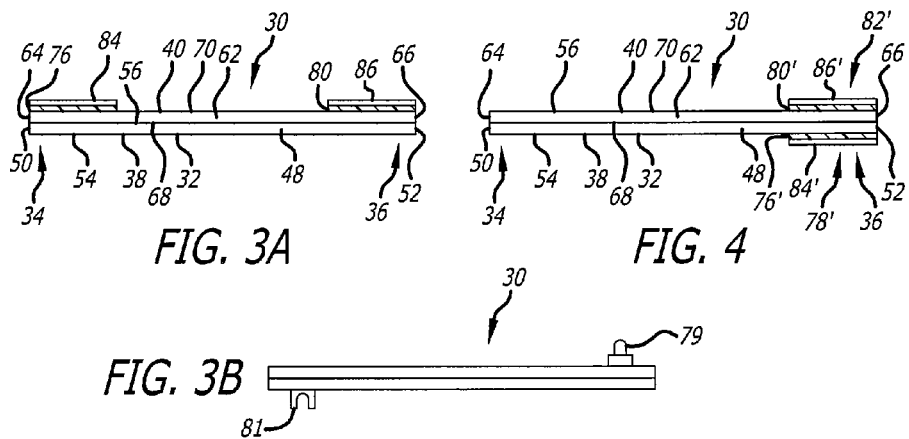
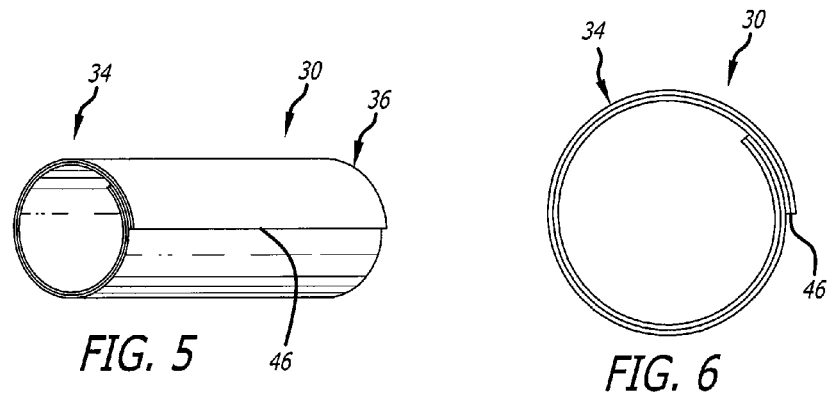

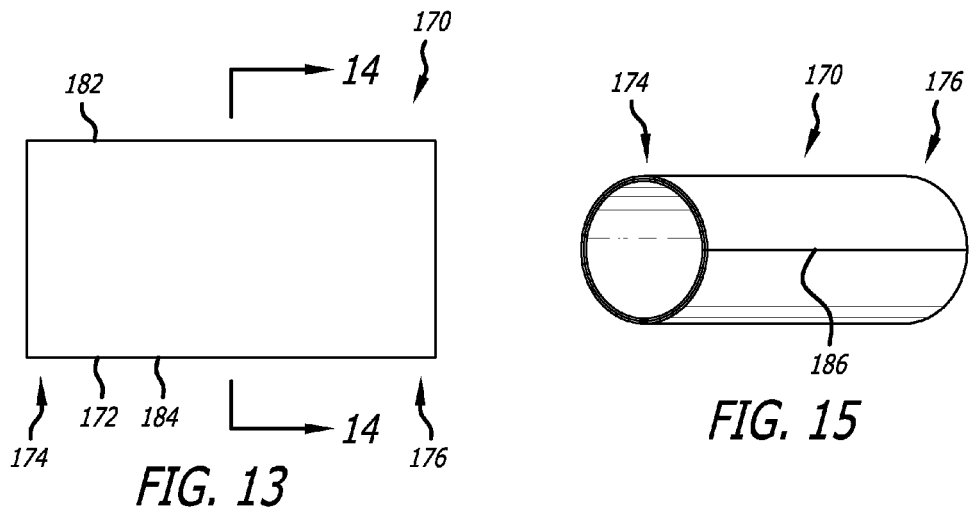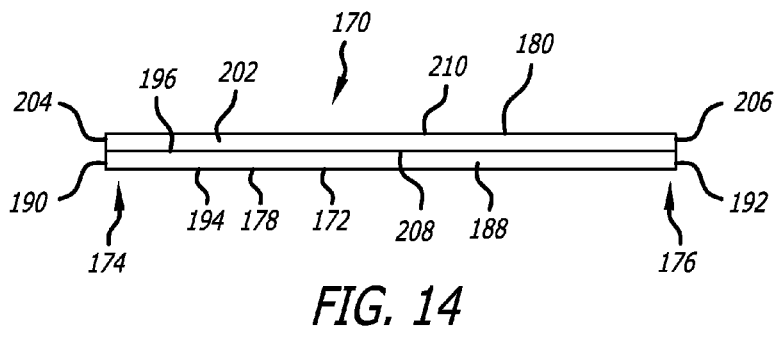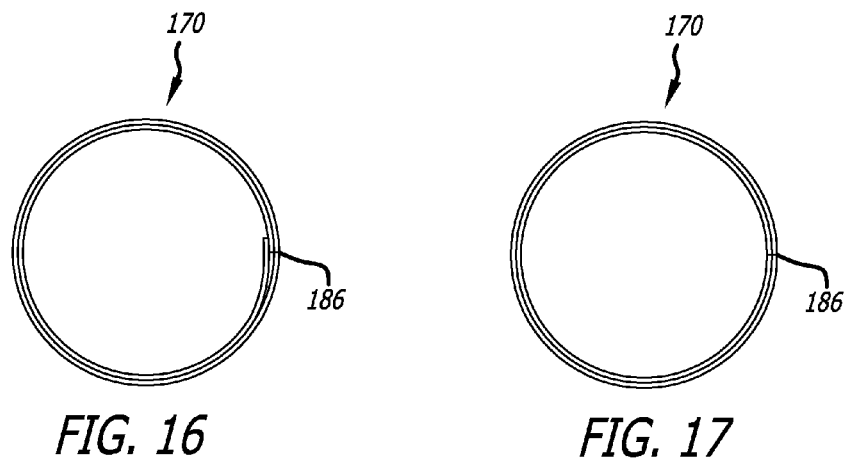

TRIPLE LAYER PROTECTIVE LINER FOR USE WITH BLOOD PRESSURE CUFF

BACKGROUND OF THE INVENTION

The present invention relates generally to the use of blood pressure cuffs of devices for blood pressure measurement, and more particularly relates to a protective liner for use with such blood pressure cuffs.

Blood pressure measurements commonly have been made by indirect methods of auscultation and oscillometry. Traditionally during blood pressure measurement, a blood pressure cuff would be placed around the upper arm of a person, inflated to a maximum pressure, and gradually deflated, while the pulse of a person was monitored at the site with a stethoscope applied directly on the person's skin to detect the person's pulse in order to determine the person's systolic and diastolic blood pressure readings. Automatic blood pressure measuring devices typically automatically inflate a blood pressure cuff once it is applied over a person's upper arm, and determine the person's systolic and diastolic blood pressure readings by detecting the person's pulse from oscillations of pressure in the blood pressure cuff. Thus, when a person's blood pressure is taken, a blood pressure cuff connected to a blood pressure measurement device is commonly placed around the person's upper arm in direct contact with the person's skin, to minimize any damping of the person's pulse or other interference with detection of a person's pulse that might otherwise occur if the blood pressure cuff were placed over the person's clothing.

Since such a blood pressure cuff can be used for taking the blood pressure of a number of people without sterilization of the blood pressure cuff prior to each usage, this practice can result in cross-contamination. Cross-contamination from blood pressure cuffs is a common problem, as recent studies have noted that outbreaks of hospital acquired infections have been traced to blood pressure cuffs. The traditional blood pressure cuff typically directly contacts a patient's skin, and use of the same blood pressure cuff sequentially on as many as thousands of different patients can readily spread infections. One solution to this problem that has been proposed is to provide each particular patient with a disposable blood pressure cuff for use only with that patient. However, single use disposable blood pressure cuffs can be prohibitively expensive.

Application of a blood pressure cuff to a person's skin can cause bruising, tearing or degradation of the person's skin. Open wounds or skin infections can be aggravated, and direct contact with the person's skin can result in an accumulation of moisture and soiling of the blood pressure cuff. In addition, when a blood pressure cuff is left in place over a person's upper arm for long term monitoring of the person's blood pressure, such as in an intensive care unit, accumulation of moisture between the blood pressure cuff and the person's skin can cause undesirable softening and degradation of the person's skin.

One known type of disposable liner for use with standard blood pressure cuffs of blood pressure measuring devices to reduce possible cross-contamination is secured to the inside of the blood pressure cuff, and disposed of after each use. The disposable liner includes an inner layer of a non-woven web, a middle layer of absorbent material, an outer layer of vapor-proof plastic, and a low-tack adhesive applied to the outer layer allowing the liner to be temporarily secured to the inside of the blood pressure cuff. Another known type of protective covering for a sphygmomanometer cuff includes a flexible material sleeve defining a pouch for containing a blood pressure cuff. The sleeve is structured for fastening about a person's arm. Another type of protective sleeve for a sphygmomanometer cuff is also known that is formed as an elongated flexible envelope for receiving a blood pressure cuff. A splashproof, adjustable limb sleeve is also known that can be placed over a limb of a person. The sleeve is made from a material that absorbs moisture from the person's skin, and repels moisture from the outside. The sleeve includes an adjustable silicone seal that is sewn to each end of the protective sleeve to provide a splashproof closure between the limb and the sleeve. The sleeve is fastened around the limb by a hook and loop fastener.

It would be desirable to provide a protective liner that can be placed around the upper arm of a person and used multiple times with the individual person with a common blood pressure cuff, to protect the skin of the person, to wick moisture away from the person's skin to help prevent degradation of the person's skin, and to provide a moisture permeable, microporous microbial barrier to substantially prevent cross-contamination from repeated use of the blood pressure cuff with a number of persons.

A potential problem with liners and sleeves for use with blood pressure cuffs, particularly liners or sleeves having a thick absorbent layer, is possible interference by such liners or sleeves with detection of a person's systolic and diastolic blood pressure readings. However, recent studies have shown that differences in mean blood pressure readings taken with a cuff placed over a subject's shirt sleeve and taken over a subject's unclothed, bare arm were not significant, and were not clinically important, so that it is possible for an appropriate liner or sleeve of comparable thickness to a shirt sleeve to be suitable for use with a blood pressure cuff. It would be desirable to provide a protective liner for use with a blood pressure cuff that permits detection of a person's pulse through the protective liner, substantially without interference with measurement of the person's blood pressure. The present invention addresses these and other needs.

SUMMARY OF THE INVENTION

Briefly, and in general terms, the present invention provides for a protective liner for use with a blood pressure measuring cuff, wherein the protective liner includes multiple layers of material configured to protect the skin of the person, wick moisture away from the person's skin, and provide a moisture permeable, microporous microbial barrier. The protective liner is porous and sufficiently thin so that the protective liner will not substantially interfere with detection of a person's pulse through the protective liner and a blood pressure cuff. The multiple layers of material are configured to permit passage of water vapor therethrough while substantially preventing passage of microbes therethrough.

Accordingly, the present invention provides for a protective liner for use with a blood pressure measuring cuff on a person's arm, the protective liner being formed of a plurality of layers of material, including a first layer of material formed of woven fabric, and a second layer of material joined to the first layer of material and formed of a porous polymeric film having pores therethrough configured to permit passage of water vapor therethrough while substantially preventing passage of microbes therethrough. In a presently preferred aspect, the first layer of material is formed of a woven fabric selected from the group consisting of natural woven fabrics and synthetic woven fabrics, and is preferably formed of silk.

In another presently preferred aspect, the porous polymeric film can be a microporous film such as a polyolefin, thermoplastic elastomer, thermoset elastomer, polyurethane, polyethylene, polypropylene or blends thereof. The microporous film typically has pores therein having a diameter less than or equal to 0.027 µm, and has a thickness of about 0.002 inches or less, and preferably in the range of from about 0.0005 inch (0.00127 cm) to about 0.002 inch (0.00508 cm).

In a presently preferred aspect, a third layer of material formed of a nonabsorbent wicking material can be interposed between the first and second layers of material, and the first, second and third layers of material together form the multilayer protective sheet material. In another presently preferred aspect, the nonabsorbent wicking material is a hydrophobic material, which can be a natural hydrophobic fabric, such as cotton, wool, silk and linen treated with a water repellent agent, for example, or a synthetic hydrophobic fabric, such as polyester, polypropylene, polyamide or microfiber material, for example. In another aspect, the first and second ends of the multilayer protective sheet material can be permanently joined together to form a tubular liner.

In one presently preferred aspect, a first area adjacent to the first end of the first planar side of the multilayer protective sheet material can include a first low-tack adhesive portion, and a second low-tack adhesive portion can be applied to a second area adjacent to the second end of the first planar side of the multilayer protective sheet material. Alternatively, a first area adjacent to the first end of the first planar side of the multilayer protective sheet material can include a first low-tack adhesive portion, and a second area adjacent to the first end of the second planar side of the multilayer protective sheet material can include a second low-tack adhesive portion. In another presently preferred aspect, a first peelable covering can be removably affixed over the first low-tack adhesive, and a second peelable covering can be removably affixed over the second low-tack adhesive. In one presently preferred variation, one or more tongue and groove seal assemblies can be provided on at least one of the opposing first and second side edges the surface of the protective liner, including a tongue portion on the surface of the second end of the protective liner removably engageable with a corresponding groove portion on the corresponding opposing surface of the first end of the protective liner. In another presently preferred variation, the protective liner can include a high friction or non-slip material on a first area adjacent to the first end of the first planar side of the multilayer protective sheet material, or a high friction or non-slip material applied to a first area adjacent to the second end of the second planar side of the multilayer protective sheet material.

These and other aspects and advantages of the invention will become apparent from the following detailed description and the accompanying drawings, which illustrate by way of example the features of the invention.

BRIEF DESCRIPTION OF THE DRAWINGS

FIG. 1 is a top plan view of a first embodiment of the protective liner for use with a blood pressure measuring cuff, according to the invention.

FIG. 2 is a top plan view of a variation of the first embodiment of the protective liner of FIG. 1, according to the invention.

FIG. 3A is a cross-sectional view taken along line 3-3 of FIG. 1.

FIG. 3B is a cross-sectional view similar to FIG. 3A illustrating another variation of the first embodiment.

FIG. 4 is a cross-sectional view taken along line 4-4 of FIG. 2.

FIG. 5 is a perspective view of the protective liner of FIG. 1 or FIG. 2, with the ends of the protective liner joined to form a tubular protective liner, according to the invention.

FIG. 6 is an end view of the protective liner of FIG. 5.

FIG. 13 is a top plan view of a third embodiment of the protective liner for use with a blood pressure measuring cuff, according to the invention.

FIG. 14 is a cross-sectional view taken along line 14-14 of FIG. 13.

FIG. 15 is a perspective view of the protective liner of FIG. 13, with opposing ends of the protective liner joined to form a tubular protective liner, according to the invention.

FIG. 16 is an end view of the tubular protective liner of FIG. 15, shown formed with the opposing ends of the first layer overlapping and joined together.

FIG. 17 is an end view of the tubular protective liner of FIG. 15, shown formed with the opposing ends of the first and second layers of material joined together and contiguous.

DETAILED DESCRIPTION OF THE PREFERRED EMBODIMENTS

Figures 7, 8:
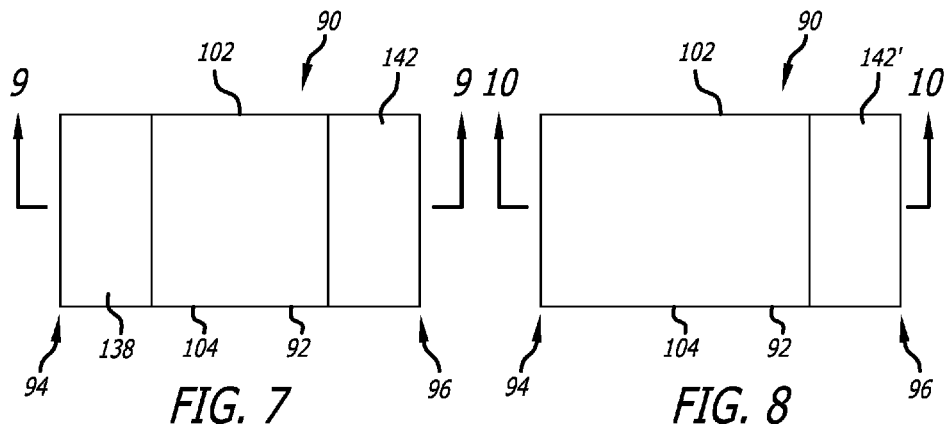
FIG. 7 is a top plan view of a second embodiment of the protective liner for use with a blood pressure measuring cuff, according to the invention.
FIG. 8 is a top plan view of a variation of the second embodiment of the protective liner of FIG. 7, according to the invention.

With reference to the drawings, which are provided by way of example, and not by way of limitation, in a first embodiment, the present invention accordingly provides for a protective liner 30 for use with a blood pressure measuring cuff (not shown) on a person's arm (not shown). Referring to FIGS. 1-6, the protective liner is preferably formed from a multilayer sheet of material 32, having first and second opposing ends 34, 36, first and second planar sides 38, 40, and first and second opposing side edges 42, 44. The first and second opposing ends can be joined together, such as by adhesive, heat sealing, or by being sewn together, for example, to form the protective liner in a tubular shape, and forming an outer seam 46.

The multilayer sheet of material includes a first layer of material 48 forming the first planar side of the multilayer sheet formed of a soft, woven fabric adapted to contact and protect a person's skin, and having pores therein configured to permit passage of water vapor through the first layer of material, to allow for wicking away of moisture from a person's skin through the first inner layer. The first layer of material includes first and second ends 50, 52, first and second planar sides 54, 56, and first and second side edges 58, 60. The first layer of material is preferably formed of a woven fabric selected from the group consisting of natural woven fabrics and synthetic woven fabrics, and is currently most preferably formed of silk, which also has wicking properties. One silk fabric that may be suitable for use with the invention is an antimicrobial silk fabric available under the trademark "DERMASILK" from Espere Healthcare Ltd. of the United Kingdom. The first layer of material preferably has a thickness of about 3 mil (about 0.008 cm) to about 8 mil (about 0.020 cm).

The multilayer sheet also includes a second layer of material 62 forming the second planar side of the multilayer sheet. The second layer of material forms a breathable, microporous barrier to microorganisms permitting the passage and evaporation of water vapor through the multilayer sheet. The second layer of material includes first and second ends 64, 66, first and second planar sides 68, 70, and first and second side edges 72, 74. The first and second ends and the first and second side edges of the first and second layers of material preferably are contiguous, and preferably together form the multilayer protective sheet material. The first and second layers of material are preferably joined together, typically at least along their peripheral edges, such as by adhesive or heat sealing, or are sewn together, for example.

The second layer of material is preferably formed of a porous polymeric film having pores therethrough configured to permit passage of water vapor therethrough while substantially preventing passage of microbes therethrough. The porous polymeric film can be a microporous film such as a polyolefin, thermoplastic elastomer, thermoset elastomer, polyurethane, polyethylene, polypropylene or blends thereof, for example. The microporous film typically has pores therein having a mean diameter approximately less than or equal to 0.027 µm, and has a thickness of about 4 mil (about 0.01 cm) or less, and more preferably has a thickness in the range of about 0.5 mil (about 0.00127 cm) to about 2 mil (about 0.00508 cm). Porous polymeric materials that may be suitable for use as the porous polymeric film of the invention include a porous polymeric material available from 3M under the brand name "Micropore Paper Tape," typically having a thickness of approximately 4 mils, and a microporous hypoallergenic material available from Smith & Nephew under the brand name "Albupore™."

Referring to FIG. 3A, a first low-tack adhesive portion 76 optionally can be applied to a first area 78 adjacent to the first end of the first planar side of the multilayer sheet, and a second low-tack adhesive portion 80 optionally can be applied to a second area 82 adjacent to the second end of the first planar side of the multilayer sheet. The term "low-tack adhesive" is defined herein as an adhesive having an adhesion of between about 0.07 to about 0.5 N/cm width (about 7.1 to about 51.0 g/cm width), and preferably between about 0.15 to about 0.3 N/cm width (about 15.2 to about 30.6 g/cm width), or even less than 0.07 N/cm width (less than 7.1 g/cm width) for the first low-tack adhesive portion that may be adhered to a person's skin. Adhesion as measured herein is determined in accordance with the PSTC-1 Peel Adhesion Test conducted at a removal angle of 180° from a patient's skin or other substrate, as modified for purposes of applying the protective liner to a patient's skin, as is described in U.S. Pat. No. 5,908,693, which is incorporated by reference herein. Adhesives with an adhesion less than about 0.01 N/cm width (about 1.0 g/cm width) tend to peel prematurely from the skin, and adhesives with an adhesion more than about 0.5 N/cm width (about 51.0 g/cm width) can irritate or even tear a patient's skin upon removal of the protective liner from the patient's skin. Adhesives that may be suitable for use as low-tack adhesives are described in U.S. Pat. Nos. 6,171,985; 6,368,687; 5,908,693; 5,891,957; 7,718,241; 5,648,136; 7,097,040; 6,572,600; and 6,479,073; each of which is incorporated by reference herein. A first peelable covering 84 is removably affixed over the first low-tack adhesive portion, and a second peelable covering 86 is removably affixed over the second low-tack adhesive portion. The first peelable cover can be removed and the first low-tack adhesive portion lightly adhered to a person's arm or other limb to which a blood pressure monitor is to be affixed, while the other end of the multilayer sheet is wrapped around the person's arm or other limb. The second peelable cover can be removed, and the second low-tack adhesive portion on the second end of the multilayer sheet can then be lightly adhered to the first end of the multilayer sheet to form the protective liner in a tubular shape around the person's arm or other limb.

In a first presently preferred variation illustrated in FIG. 3B, no first low-tack adhesive portion is applied to the protective liner, and the second low-tack adhesive portion and second peelable covering may be replaced by one or more tongue and groove seal assemblies, such as two edge tongue and groove assemblies at the opposing first and second side edges, each including a tongue portion 79 on one surface of a second end of the protective liner that is removably engageable with a corresponding groove portion 81 on a corresponding opposing surface of a first end of the protective liner. The one or more tongue and groove seal assemblies can be formed of a flexible plastic material, and can be bonded to the protective liner, for example. The protective liner can be loosely wrapped around a person's arm or other limb, and the first and second ends can be joined together by pinching the one or more tongue and groove assemblies together. In another variation, the first low-tack adhesive portion can be replaced with a high friction or non-slip material such as a non-irritating, low trauma rubber, latex or vinyl material, for example, to loosely grip a patient's skin without adhering the protective liner to the patient's skin, in order to minimize potential trauma to the patient's skin.

Alternatively, in another variation illustrated in FIG. 4, a first low-tack adhesive portion 76' can be applied to a first area 78' adjacent to the first end of the first planar side of the multilayer sheet, and a second low-tack adhesive portion 80' can be applied to a second area 82' adjacent to the first end of the second planar side of the multilayer sheet. A first peelable covering 84' is removably affixed over the first low-tack adhesive portion, and a second peelable covering 86' is removably affixed over the second low-tack adhesive portion. The first peelable cover can be removed and the first low-tack adhesive portion lightly adhered to a person's arm or other limb to which a blood pressure monitor is to be affixed, while the other end of the multilayer sheet is wrapped around the person's arm or other limb. The second peelable cover can be removed, and the second low-tack adhesive portion on the second end of the multilayer sheet can then be lightly adhered to the first end of the multilayer sheet to form the protective liner in a tubular shape around the person's arm or other limb. In another variation, the first low-tack adhesive portion can be replaced with a high friction or non-slip material such as a non-irritating, low trauma rubber, latex or vinyl material, for example, to loosely grip a patient's skin without adhering the protective liner to the patient's skin, in order to minimize potential trauma to the patient's skin.

Referring to FIGS. 7-12, the present invention provides for a second embodiment of a protective liner 90 for use with a blood pressure measuring cuff (not shown) on a person's arm (not shown). The protective liner is preferably formed from a multilayer sheet of material 92, having first and second opposing ends 94, 96, first and second planar sides 98, 100, and first and second opposing side edges 102, 104. The first and second opposing ends can be joined together, such as by adhesive, heat sealing, or by being sewn together, for example, to form the protective liner in a tubular shape, and forming an outer seam 106.

The multilayer sheet of material includes a first layer of material 108 forming the first planar side of the multilayer sheet formed of a soft, woven fabric adapted to contact and protect a person's skin, and having pores therein configured to permit passage of water vapor through the first layer of material, to allow for wicking away of moisture from a person's skin through the first inner layer. The first layer of material includes first and second ends 110, 112, first and second planar sides 114, 116, and first and second side edges 118, 120. The first layer of material is preferably formed of a woven fabric selected from the group consisting of natural woven fabrics and synthetic woven fabrics, and is currently most preferably formed of silk. The first layer of material preferably has a thickness of about 3 mil (about 0.008 cm) to about 8 mil (about 0.020 cm).

The multilayer sheet also includes a second layer of material 122 forming the second planar side of the multilayer sheet. The second layer of material forms a breathable, microporous barrier to microorganisms permitting the passage and evaporation of water vapor through the multilayer sheet. The second layer of material includes first and second ends 124, 126, first and second planar sides 128, 130, and first and second side edges 132, 134. The first and second ends and the first and second side edges of the first and second layers of material preferably are contiguous, and preferably together form the multilayer protective sheet material. The first and second layers of material are preferably joined together, typically at least along their peripheral edges, such as by adhesive or heat sealing, or are sewn together, for example.

The second layer of material is preferably formed of a porous polymeric film having pores therethrough configured to permit passage of water vapor therethrough while substantially preventing passage of microbes therethrough. The porous polymeric film can be a microporous film such as a polyolefin, thermoplastic elastomer, thermoset elastomer, polyurethane, polyethylene, polypropylene or blends thereof, for example. The microporous film typically has pores therein having a mean diameter approximately less than or equal to 0.027 μm, and has a thickness of about 4 mil (about 0.01 cm) or less, and more preferably has a thickness in the range of about 0.5 mil (about 0.00127 cm) to about 2 mil (about 0.00508 cm).

Figures 9A, 10:
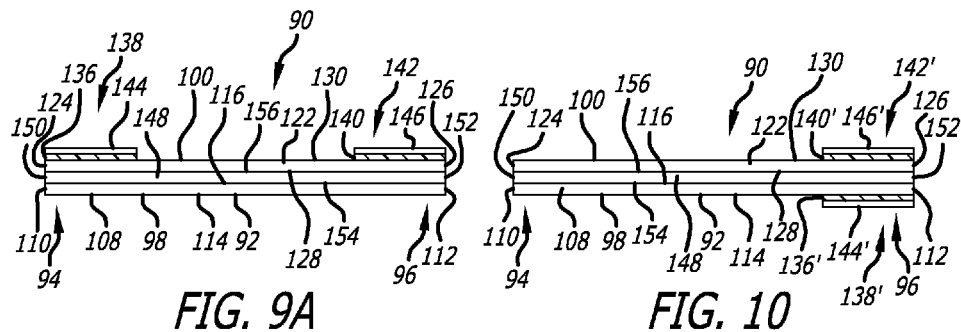
FIG. 9A is a cross-sectional view taken along line 9-9 of FIG. 7.
FIG. 10 is a cross-sectional view taken along line 10-10 of FIG. 8.
Figure 9B:
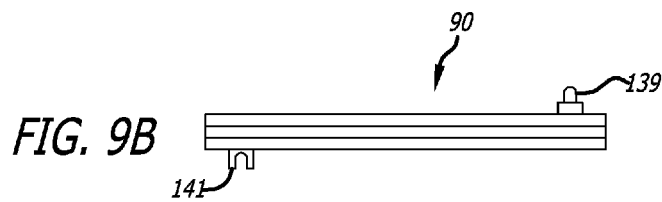
FIG. 9B is a cross-sectional view similar to FIG. 9A illustrating another variation of the second embodiment.
Figures 11, 12:
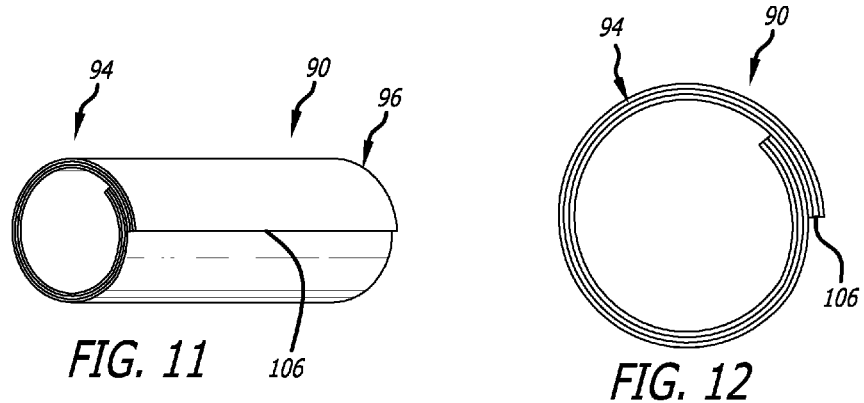
FIG. 11 is a perspective view of the protective liner of FIG. 7 or FIG. 8, with the ends of the protective liner joined to form a tubular protective liner, according to the invention.
FIG. 12 is an end view of the protective liner of FIG. 11.

Referring to FIG. 9A, a first low-tack adhesive portion 136 can be applied to a first area 138 adjacent to the first end of the first planar side of the multilayer sheet, and a second low-tack adhesive portion 140 can be applied to a second area 142 adjacent to the second end of the first planar side of the multilayer sheet. A first peelable covering 144 is removably affixed over the first low-tack adhesive portion, and a second peelable covering 146 is removably affixed over the second low-tack adhesive portion. The first peelable cover can be removed and the first low-tack adhesive portion lightly adhered to a person's arm or other limb to which a blood pressure monitor is to be affixed, while the other end of the multilayer sheet is wrapped around the person's arm or other limb. The second peelable cover can be removed, and the second low-tack adhesive portion on the second end of the multilayer sheet can then be lightly adhered to the first end of the multilayer sheet to form the protective liner in a tubular shape around the person's arm or other limb. In a first presently preferred variation illustrated in FIG. 9B, the second low-tack adhesive portion and second peelable covering may be replaced by one or more tongue and groove seal assemblies, such as two edge tongue and groove assemblies at the opposing first and second side edges, each including a tongue portion 139 on one surface of a second end of the protective liner that is removably engageable with a corresponding groove portion 141 on a corresponding opposing surface of a first end of the protective liner. The protective liner can be loosely wrapped around a person's arm or other limb, and the first and second ends can be joined together by pinching the one or more tongue and groove assemblies together. In another variation, the first low-tack adhesive portion can be replaced with a high friction or non-slip material such as a non-irritating, low trauma rubber, latex or vinyl material, for example, to loosely grip a patient's skin without adhering the protective liner to the patient's skin, in order to minimize potential trauma to the patient's skin.

Alternatively, in a variation illustrated in FIG. 10A, a first low-tack adhesive portion 136' can be applied to a first area 138' adjacent to the first end of the first planar side of the multilayer sheet, and a second low-tack adhesive portion 140' can be applied to a second area 142' adjacent to the first end of the second planar side of the multilayer sheet. A first peelable covering 144' is removably affixed over the first low-tack adhesive portion, and a second peelable covering 146' is removably affixed over the second low-tack adhesive portion. The first peelable cover can be removed and the first low-tack adhesive portion lightly adhered to a person's arm or other limb to which a blood pressure monitor is to be affixed, while the other end of the multilayer sheet is wrapped around the person's arm or other limb. The second peelable cover can be removed, and the second low-tack adhesive portion on the second end of the multilayer sheet can then be lightly adhered to the first end of the multilayer sheet to form the protective liner in a tubular shape around the person's arm or other limb. In another variation, the first low-tack adhesive portion can be replaced with a high friction or non-slip material such as a non-irritating, low trauma rubber, latex or vinyl material, for example, to loosely grip a patient's skin without adhering the protective liner to the patient's skin, in order to minimize potential trauma to the patient's skin.

Referring to FIGS. 9 and 10, a third layer of material 148 formed of a nonabsorbent wicking layer of material can be interposed between the first and second layers of material. The third layer of material has first and second ends 150, 152; first and second planar sides 154, 156; and first and second side edges 158, 160. The third layer of material is currently preferably joined to at least one of the first and second layers of material, such that the first and second ends and first and second side edges of the first, second and third layers of material are contiguous, and the first, second and third layers of material together form a multilayer protective sheet material having first and second ends and first and second side edges. Alternatively, the third layer of material may be simply contained between the first and second layers of material. The third layer is currently preferably formed of a nonabsorbent wicking material, to wick moisture away from the first layer to avoid retention of moisture that can otherwise lead to softening and degradation of the person's skin when left in place on a person's skin for long term monitoring of blood pressure. The nonabsorbent wicking material is preferably a hydrophobic material, which can be a hydrophobic natural fabric, or a synthetic hydrophobic fabric, for example. Hydrophobic natural fabrics that are suitable in the present invention are natural fabrics such as cotton, wool, silk and linen, for example, treated with a water repellent agent, such as a polyorganosiloxane composition or fluorochemical composition, which are well known in the art. Synthetic hydrophobic fabrics that are suitable in the present invention are polyester or polypropylene, for example. Wicking materials that may be suitable for use with the invention are a treated polyester fabric available under the trademark "CAPILENE" from Patagonia, and a water-repelling polyester fabric available under the trademark "COOLMAX" from Dupont. The third layer of material currently preferably has a thickness of about 13 mil (about 0.033 cm) to about 20 mil (about 0.0508 cm).

Referring to FIGS. 13-17, the present invention also provides for a third embodiment of a protective liner 170 for use with a blood pressure measuring cuff (not shown) on a person's arm (not shown). The protective liner is preferably formed from a multilayer sheet of material 172, having first and second opposing ends 174, 176; first and second planar sides 178, 180; first and second opposing side edges 182, 184. The first and second opposing ends can be joined together, such as by adhesive, heat sealing, or by being sewn together, for example, to form the protective liner in a tubular shape, with the first planar side of the multilayer sheet forming a radially inner side of the protective liner, and forming an outer seam 186.

The multilayer sheet of material includes a first layer of material 188 forming the first planar side of the multilayer sheet formed of a soft, woven fabric adapted to contact and protect a person's skin, and having pores therein configured to permit passage of water vapor through the first layer of material, to allow for wicking away of moisture from a person's skin through the first inner layer. The first layer of material includes first and second ends 190, 192, first and second planar sides 194, 196, and first and second side edges 198, 200. The first layer of material is preferably formed of a woven fabric selected from the group consisting of natural woven fabrics and synthetic woven fabrics, and is currently most preferably formed of silk. The first layer of material preferably has a thickness of about 3 mil (about 0.008 cm) to about 8 mil (about 0.020 cm).

The multilayer sheet also includes a second layer of material 202 forming the second planar side of the multilayer sheet. The second layer of material forms a breathable, microporous barrier to microorganisms permitting the passage and evaporation of water vapor through the multilayer sheet. The second layer of material includes first and second ends 204, 206, first and second planar sides 208, 210, and first and second side edges 212, 214. The first and second ends and the first and second side edges of the first and second layers of material preferably are contiguous, and preferably together form the multilayer protective sheet material. The first and second layers of material are preferably joined together, typically at least along their peripheral edges, such as by adhesive or heat sealing, or are sewn together, for example.

The second layer of material is preferably formed of a porous polymeric film having pores therethrough configured to permit passage of water vapor therethrough while substantially preventing passage of microbes therethrough. The porous polymeric film can be a microporous film such as a polyolefin, thermoplastic elastomer, thermoset elastomer, polyurethane, polyethylene, polypropylene or blends thereof, for example. The microporous film typically has pores therein having a mean diameter approximately less than or equal to 0.027 µm, and has a thickness of about 4 mil (about 0.01 cm) or less, and more preferably has a thickness in the range of about 0.5 mil (about 0.00127 cm) to about 2 mil (about 0.00508 cm). A low-tack adhesive optionally may also be applied to the first planar side of the multilayer sheet of material, such that the low-tack adhesive is on the radially inner side of the multilayer sheet material formed into a tubular shape, to lightly removably adhere the protective liner to a person's skin, and help retain the protective liner in place on the person's arm or other limb before application of a blood pressure cuff over the protective liner.

As is illustrated in FIGS. 13 and 14, the first and second ends and first and second side edges of the first and second layers forming the multilayer protective sheet material are preferably contiguous, and the opposing first and second ends of the multilayer protective sheet material are preferably joined together to form the protective liner in a tubular shape. As is illustrated in FIG. 16, the tubular protective liner can be formed by overlapping and sewing the opposing ends of the first layer of material together, although the opposing ends can alternatively be heat sealed together, or bonded together with adhesive. As is illustrated in FIGS. 16 and 17, the opposing ends of the second layer of material are preferably bonded together to form a permanent seal, such as by heat sealing, or by being bonded together with adhesive, so as to form a barrier that is substantially impermeable to microbes. As is illustrated in FIG. 17, the opposing ends of the multilayer protective sheet material can be permanently joined together, such as by being bonded together with adhesive, or by being heat sealed together, for example.

Referring to FIGS. 18-22, the present invention also provides for a fourth embodiment of a protective liner 220 for use with a blood pressure measuring cuff (not shown) on a person's arm (not shown). The protective liner is preferably formed from a multilayer sheet of material 222, having first and second opposing ends 224, 226; first and second planar sides 228, 230; and first and second opposing side edges 232, 234. The first and second opposing ends can be joined together, such as by adhesive, heat sealing, or by being sewn together, for example, to form the protective liner in a tubular shape, with the first planar side of the multilayer sheet forming a radially inner side of the protective liner, and forming an outer seam 236.

The multilayer sheet of material includes a first layer of material 238 forming the first planar side of the multilayer sheet formed of a soft, woven fabric adapted to contact and protect a person's skin, and having pores therein configured to permit passage of water vapor through the first layer of material, to allow for wicking away of moisture from a person's skin through the first inner layer. The first layer of material includes first and second ends 240, 242, first and second planar sides 244, 246, and first and second side edges 248, 250. The first layer of material is preferably formed of a woven fabric selected from the group consisting of natural woven fabrics and synthetic woven fabrics, and is currently most preferably formed of silk. The first layer of material preferably has a thickness of about 3 mil (about 0.008 cm) to about 8 mil (about 0.020 cm).

The multilayer sheet also includes a second layer of material 252 forming the second planar side of the multilayer sheet. The second layer of material forms a breathable, microporous barrier to microorganisms permitting the passage and evaporation of water vapor through the multilayer sheet. The second layer of material includes first and second ends 254, 256; first and second planar sides 258, 260; and first and second side edges 262, 264. The first and second ends and the first and second side edges of the first and second layers of material preferably are contiguous, and preferably together form the multilayer protective sheet material. The first and second layers of material are preferably joined together, typically at least along their peripheral edges, such as by adhesive or heat sealing, or are sewn together, for example.

The second layer of material is preferably formed of a porous polymeric film having pores therethrough configured to permit passage of water vapor therethrough while substantially preventing passage of microbes therethrough. The porous polymeric film can be a microporous film such as a polyolefin, thermoplastic elastomer, thermoset elastomer, polyurethane, polyethylene, polypropylene or blends thereof, for example. The microporous film typically has pores therein having a mean diameter approximately less than or equal to 0.027 µm, and has a thickness of about 4 mil (about 0.01 cm) or less, and more preferably has a thickness in the range of about 0.5 mil (about 0.00127 cm) to about 2 mil (about 0.00508 cm). A low-tack adhesive optionally may also be applied to the first planar side of the multilayer sheet of material, such that the low-tack adhesive is on the radially inner side of the multilayer sheet material formed into a tubular shape, to lightly removably adhere the protective liner to a person's skin, and help retain the protective liner in place on the person's arm or other limb before application of a blood pressure cuff over the protective liner.

The protective liner formed from the multilayer sheet of material also includes a third layer of material 266 formed of a nonabsorbent wicking layer of material that can be interposed between the first and second layers of material. The third layer of material has first and second ends 268, 270; first and second planar sides 272, 274; and first and second side edges 276, 278. The third layer of material is currently preferably joined to at least one of the first and second layers of material, such that the first and second ends and first and second side edges of the first, second and third layers of material are contiguous, and the first, second and third layers of material together form a multilayer protective sheet material having first and second ends and first and second side edges. Alternatively, the third layer of material may be simply contained between the first and second layers of material. The third layer is currently preferably formed of a nonabsorbent wicking material, to wick moisture away from the first layer to avoid retention of moisture that can otherwise lead to softening and degradation of the person's skin when left in place on a person's skin for long term monitoring of blood pressure. The nonabsorbent wicking material is preferably a hydrophobic material, which can be a hydrophobic natural fabric, or a synthetic hydrophobic fabric, for example. Examples of hydrophobic natural fabrics that are suitable in the present invention are natural fabrics such as cotton, wool, silk and linen, for example, treated with a water repellent agent, such as a polyorganosiloxane composition or fluorochemical composition, which are well known in the art. Examples of synthetic hydrophobic fabrics that are suitable in the present invention are polyester or polypropylene, for example. The third layer of material currently preferably has a thickness of about 13 mil (about 0.033 cm) to about 20 mil (about 0.0508 cm).

Figure 18:
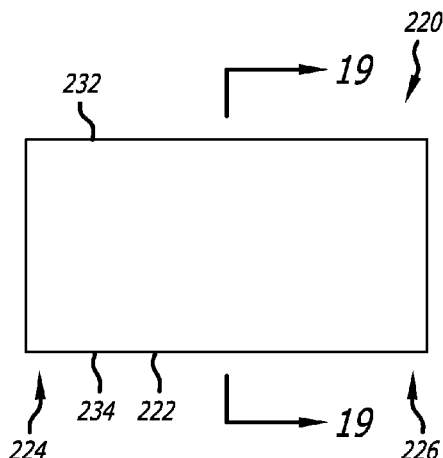
FIG. 18 is a top plan view of a fourth embodiment of the protective liner for use with a blood pressure measuring cuff, according to the invention.
Figure 20:
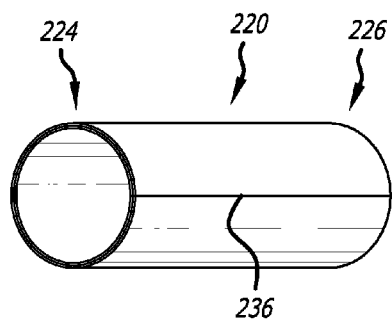
FIG. 20 is a perspective view of the protective liner of FIG. 18, with opposing ends of the protective liner joined to form a tubular protective liner, according to the invention.
Figure 19:
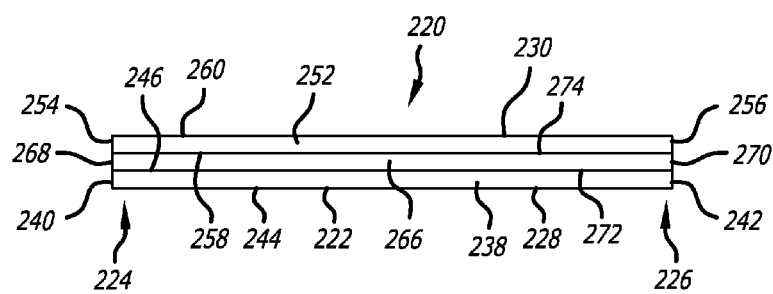
FIG. 19 is a cross-sectional view taken along line 19-19 of FIG. 18.
Figure 21:
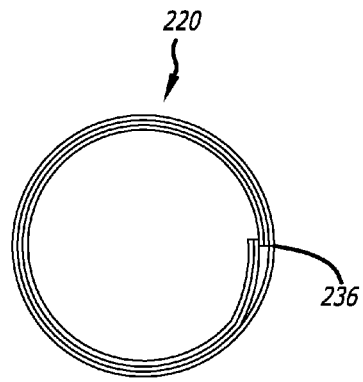
FIG. 21 is an end view of the tubular protective liner of FIG. 20, shown formed with the opposing ends of the first and third layers overlapping and joined together.
Figure 22:
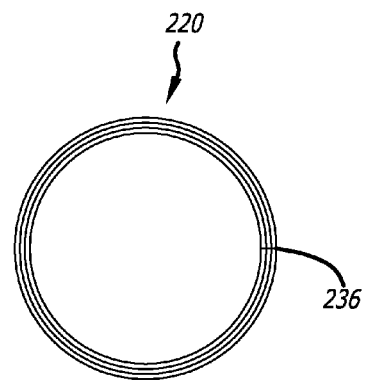
FIG. 22 is an end view of the tubular protective liner of FIG. 20, shown formed with the opposing ends of the first, second and third layers of material joined together and contiguous.

As is illustrated in FIGS. 18 and 19, the first and second ends and first and second side edges of the first and second layers forming the multilayer protective sheet material are preferably contiguous, and the opposing first and second ends of the multilayer protective sheet material are preferably joined together to form the protective liner in a tubular shape. As is illustrated in FIG. 22, the tubular protective liner can be formed by overlapping and sewing the opposing ends of the first and third layers of material together, although the opposing ends can alternatively be heat sealed together, or bonded together with adhesive. Alternatively, the tubular protective liner can be formed by overlapping and sewing the opposing ends of the first, radially inner layer of material together, although the opposing ends can alternatively be heat sealed together, or bonded together with adhesive; and the opposing ends of the second, middle layer of material can be overlapped and sewn together, heat sealed together, or bonded together with adhesive. As is illustrated in FIGS. 21 and 22, the opposing ends of the second layer of material are preferably joined together to form a permanent seal, such as by heat sealing, or by being bonded together with adhesive, so as to form a barrier that is substantially impermeable to microbes. As is illustrated in FIG. 22, the opposing ends of the multilayer protective sheet material can be permanently joined together, such as by being bonded together with adhesive, or by being heat sealed together, for example.

It will be apparent from the foregoing that while particular forms of the invention have been illustrated and described, various modifications can be made without departing from the spirit and scope of the invention. It should be noted that the length and width of blood pressure cuffs can vary widely, from as small as 3 to 6 cm for an infant, to as large as 42-50 inches to fit a large adult's thigh, so that the length and width of the protective liner of the present invention can also vary widely as needed. Accordingly, it is not intended that the invention be limited, except as by the appended claims.

I claim:

1. A protective liner for use with a blood pressure measuring cuff on a person's arm, comprising:
    a first layer of material formed of woven fabric adapted to contact and protect a person's skin, said first layer of material having pores therethrough configured to permit passage of water vapor therethrough, and having first and second ends, first and second planar sides, and first and second side edges;
    a second layer of material formed of a porous polymeric film having pores having a diameter less than or equal to 0.027 µm therethrough configured to permit passage of water vapor therethrough while substantially preventing passage of microbes therethrough, and having first and second ends, first and second planar sides, and first and second side edges, said second layer of material being joined to said first layer of material, and said first and second layers of material together forming a multilayer protective sheet material having first and second ends, first and second planar sides, and first and second side edges; and a
    third layer of material interposed between said first and second layers of material, said third layer being formed of a nonabsorbent wicking material, and said first, second and third layers of material together forming said multilayer protective sheet material, such that when the protective liner is applied over the skin of the person's arm, the protective liner is configured to wick moisture away from the skin of the person's arm; and
    a first low-tack adhesive portion applied to a first area of said first layer of material adjacent to said second end of said first planar side of said multilayer protective sheet material, said first low-tack adhesive portion being configured to be removably adhered to the skin of the person's arm, and a second low-tack adhesive portion applied to a second area of said second layer of material adjacent to said second end of said second planar side of said multilayer protective sheet material, said second low-tack adhesive portion being configured to be removably adhered to said first end of said multilayer protective sheet material, the protective liner having a total thickness range between 16 mils to 32 mils to provide substantially no interference with blood pressure detection through the protective liner with the blood pressure measuring cuff.

2. The protective liner of claim 1, wherein said first layer of material comprises a woven fabric selected from the group consisting of natural woven fabrics and synthetic woven fabrics.

3. The protective liner of claim 1, wherein said first layer of material is silk.

4. The protective liner of claim 1, wherein said porous polymeric film comprises a microporous film selected from the group of polymers consisting of polyolefins, thermoset elastomers, polyurethanes, polyethylenes, polypropylenes and blends thereof.

5. The protective liner of claim 1, further comprising a first peelable covering removably affixed over said first low-tack adhesive, and a second peelable covering removably affixed over said second low-tack adhesive.

6. The protective liner of claim 1, wherein said first and second ends and first and second side edges of said first and second layers of material are contiguous.

7. The protective liner of claim 1, wherein said first and second ends of said multilayer protective sheet material are removably joined together to form a tubular liner.

8. The protective liner of claim 1, wherein said third layer of material is joined to at least one of said first and second layers of material.

9. The protective liner of claim 1, wherein said nonabsorbent wicking material comprises a hydrophobic material selected from the group consisting of natural hydrophobic fabric and synthetic hydrophobic fabric.

10. The protective liner of claim 9, wherein said synthetic hydrophobic fabric is selected from the group consisting of polyester and polypropylene.

11. The protective liner of claim 9, wherein said natural hydrophobic fabric is formed from a natural fabric treated with a water repellent agent.

12. A protective liner for use with a blood pressure measuring cuff on a person's arm, comprising:
 a first layer of material formed of woven fabric adapted to contact and protect a person's skin, said first layer of material having pores therethrough configured to permit passage of water vapor therethrough, and having first and second ends, first and second planar sides, and first and second side edges;
 a second layer of material formed of a porous polymeric film having pores having a diameter less than or equal to 0.027 μm therethrough configured to permit passage of water vapor therethrough while substantially preventing passage of microbes therethrough, and having first and second ends, first and second planar sides, and first and second side edges, said second layer of material being joined to said first layer of material, and said first and second layers of material together forming a multilayer protective sheet material having first and second ends, first and second planar sides, and first and second side edges; and a
 third layer of material interposed between said first and second layers of material, said third layer being formed of a nonabsorbent wicking material, and said first, second and third layers of material together forming said multilayer protective sheet material, such that when the protective liner is applied over the skin of the person's arm, the protective liner is configured to wick moisture away from the skin of the person's arm; and
 a non-slip high friction material applied to a first area adjacent to said second end of said first planar side of said multilayer protective sheet material, said non-slip high friction material being configured to grip the skin of the person's arm without slipping and without adhering the protective liner to the skin of the person's arm, and a low-tack adhesive portion applied to a second area of said second layer of material adjacent to said second end of said second planar side of said multilayer protective sheet material, said low-tack adhesive portion being configured to be removably adhered to said first end of said multilayer protective sheet material, the protective liner having a total thickness range between 16 mils to 32 mils to provide substantially no interference with blood pressure detection through the protective liner with the blood pressure measuring cuff.

13. The protective liner of claim 12, wherein said first layer of material comprises a woven fabric selected from the group consisting of natural woven fabrics and synthetic woven fabrics.

14. The protective liner of claim 12, wherein said first layer of material is silk.

15. The protective liner of claim 12, wherein said porous polymeric film comprises a microporous film selected from the group of polymers consisting of polyolefins, thermoset elastomers, polyurethanes, polyethylenes, polypropylenes and blends thereof.

16. The protective liner of claim 12, wherein said first and second ends and first and second side edges of said first and second layers of material are contiguous.

17. The protective liner of claim 12, wherein said first and second ends of said multilayer protective sheet material are removably joined together to form a tubular liner.

18. The protective liner of claim 12, wherein said third layer of material is joined to at least one of said first and second layers of material.

19. The protective liner of claim 12, wherein said nonabsorbent wicking material comprises a hydrophobic material selected from the group consisting of natural hydrophobic fabric and synthetic hydrophobic fabric.

20. The protective liner of claim 12, wherein said non-slip high friction material is selected from the group consisting of non-irritating, low trauma rubber material, non-irritating, low trauma latex material and non-irritating, low trauma vinyl material, and combinations thereof.

* * * * *

UNITED STATES PATENT AND TRADEMARK OFFICE
CERTIFICATE OF CORRECTION

| | | |
|---|---|---|
| PATENT NO. | : 8,956,302 B2 | |
| APPLICATION NO. | : 12/839089 | |
| DATED | : February 17, 2015 | |
| INVENTOR(S) | : Susan L. Pollyea | |

It is certified that error appears in the above-identified patent and that said Letters Patent is hereby corrected as shown below:

Delete title page and substitute therefore with the attached page consisting of the corrected title:
--PROTECTIVE LINER FOR USE WITH BLOOD PRESSURE CUFF--.

In the Specification

Delete Column 1, line 1 through Column 2, line 67 and substitute therefore with the attached Column 1, line 1 through Column 2, line 67. The title in Column 1 has been corrected to read: --PROTECTIVE LINER FOR USE WITH BLOOD PRESSURE CUFF--.

Signed and Sealed this
Seventeenth Day of March, 2015

Michelle K. Lee
*Director of the United States Patent and Trademark Office*

(12) United States Patent
Pollyea

(10) Patent No.: US 8,956,302 B2
(45) Date of Patent: Feb. 17, 2015

(54) PROTECTIVE LINER FOR USE WITH BLOOD PRESSURE CUFF

(76) Inventor: Susan L. Pollyea, Los Angeles, CA (US)

( * ) Notice: Subject to any disclaimer, the term of this patent is extended or adjusted under 35 U.S.C. 154(b) by 334 days.

(21) Appl. No.: 12/839,089

(22) Filed: Jul. 19, 2010

(65) Prior Publication Data
US 2012/0016248 A1 Jan. 19, 2012

(51) Int. Cl.
*A61B 5/02* (2006.01)
*A61B 5/022* (2006.01)

(52) U.S. Cl.
CPC ...... *A61B 5/02233* (2013.01); *A61B 2562/247* (2013.01)
USPC .................................................. 600/499

(58) Field of Classification Search
CPC ... A61B 5/02233; A61F 13/04; A61K 9/7023
USPC .................................. 600/479, 481, 490–499
See application file for complete search history.

(56) References Cited

U.S. PATENT DOCUMENTS

| | | | | |
|---|---|---|---|---|
| 4,235,228 A | * | 11/1980 | Gaylord et al. | 602/8 |
| 4,344,999 A | * | 8/1982 | Gohlke | 128/849 |
| 4,548,249 A | | 10/1985 | Slaughterbeck | |
| 4,671,266 A | | 6/1987 | Lengyel et al. | |
| 4,966,136 A | * | 10/1990 | Bates | 602/18 |
| 4,967,758 A | | 11/1990 | Masciarotte | |
| 5,065,600 A | | 11/1991 | Byles | |
| 5,251,646 A | | 10/1993 | Bowen | |
| 5,392,782 A | * | 2/1995 | Garrett | 600/499 |
| 5,396,894 A | | 3/1995 | Eide et al. | |
| H1585 H | | 8/1996 | Alu | |
| 5,648,136 A | | 7/1997 | Bird | |
| 5,660,182 A | * | 8/1997 | Kuroshaki et al. | 600/499 |
| 5,746,213 A | * | 5/1998 | Marks | 600/499 |
| 5,780,048 A | | 7/1998 | Lee | |
| 5,875,493 A | | 3/1999 | MacDonald et al. | |
| 5,891,957 A | | 4/1999 | Hansen et al. | |
| 5,908,693 A | | 6/1999 | Delgado et al. | |
| 5,938,874 A | | 8/1999 | Palomo et al. | |
| 6,040,251 A | | 3/2000 | Caldwell | |
| 6,171,985 B1 | | 1/2001 | Joseph et al. | |
| 6,210,352 B1 | | 4/2001 | Williams et al. | |
| 6,262,330 B1 | * | 7/2001 | Fujisawa et al. | 602/54 |
| 6,364,843 B1 | * | 4/2002 | Lightle | 600/490 |
| 6,368,687 B1 | | 4/2002 | Joseph et al. | |

(Continued)

OTHER PUBLICATIONS

Kahan, Ernesto et al., Comparison of Blood Pressure Measurements on the Bare Arm, Below a Rolled-Up Sleeve, or Over a Sleeve, Oxford University Press 2003, Family Practice vol. 20, No. 6, pp. 730-732.

(Continued)

*Primary Examiner* — Jacqueline Cheng
*Assistant Examiner* — Puya Agahi
(74) *Attorney, Agent, or Firm* - - Fulwider Patton LLP

(57) ABSTRACT

A protective liner for use with a blood pressure measuring cuff includes three layers of material configured to protect a person's skin, wick moisture away from the person's skin, and provide a moisture permeable, microporous barrier to microbes. The protective liner is porous and sufficiently thin so that the protective liner will not substantially interfere with blood pressure monitoring through the protective liner. The three layers of material are configured to wick moisture therethrough away from the person's skin, while substantially preventing passage of microbes therethrough.

20 Claims, 4 Drawing Sheets

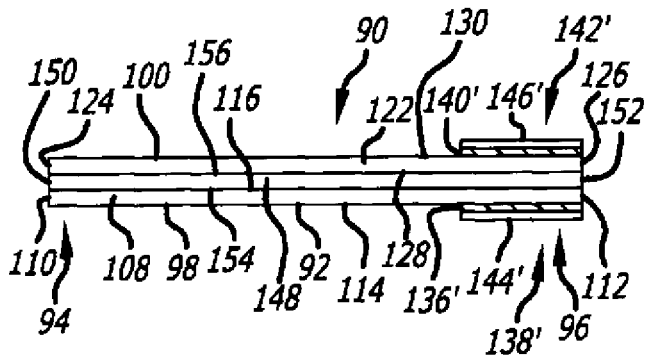

PROTECTIVE LINER FOR USE WITH BLOOD PRESSURE CUFF

BACKGROUND OF THE INVENTION

The present invention relates generally to the use of blood pressure cuffs of devices for blood pressure measurement, and more particularly relates to a protective liner for use with such blood pressure cuffs.

Blood pressure measurements commonly have been made by indirect methods of auscultation and oscillometry. Traditionally during blood pressure measurement, a blood pressure cuff would be placed around the upper arm of a person, inflated to a maximum pressure, and gradually deflated, while the pulse of a person was monitored at the site with a stethoscope applied directly on the person's skin to detect the person's pulse in order to determine the person's systolic and diastolic blood pressure readings. Automatic blood pressure measuring devices typically automatically inflate a blood pressure cuff once it is applied over a person's upper arm, and determine the person's systolic and diastolic blood pressure readings by detecting the person's pulse from oscillations of pressure in the blood pressure cuff. Thus, when a person's blood pressure is taken, a blood pressure cuff connected to a blood pressure measurement device is commonly placed around the person's upper arm in direct contact with the person's skin, to minimize any damping of the person's pulse or other interference with detection of a person's pulse that might otherwise occur if the blood pressure cuff were placed over the person's clothing.

Since such a blood pressure cuff can be used for taking the blood pressure of a number of people without sterilization of the blood pressure cuff prior to each usage, this practice can result in cross-contamination. Cross-contamination from blood pressure cuffs is a common problem, as recent studies have noted that outbreaks of hospital acquired infections have been traced to blood pressure cuffs. The traditional blood pressure cuff typically directly contacts a patient's skin, and use of the same blood pressure cuff sequentially on as many as thousands of different patients can readily spread infections. One solution to this problem that has been proposed is to provide each particular patient with a disposable blood pressure cuff for use only with that patient. However, single use disposable blood pressure cuffs can be prohibitively expensive.

Application of a blood pressure cuff to a person's skin can cause bruising, tearing or degradation of the person's skin. Open wounds or skin infections can be aggravated, and direct contact with the person's skin can result in an accumulation of moisture and soiling of the blood pressure cuff. In addition, when a blood pressure cuff is left in place over a person's upper arm for long term monitoring of the person's blood pressure, such as in an intensive care unit, accumulation of moisture between the blood pressure cuff and the person's skin can cause undesirable softening and degradation of the person's skin.

One known type of disposable liner for use with standard blood pressure cuffs of blood pressure measuring devices to reduce possible cross-contamination is secured to the inside of the blood pressure cuff, and disposed of after each use. The disposable liner includes an inner layer of a non-woven web, a middle layer of absorbent material, an outer layer of vapor-proof plastic, and a low-tack adhesive applied to the outer layer allowing the liner to be temporarily secured to the inside of the blood pressure cuff. Another known type of protective covering for a sphygmomanometer cuff includes a flexible material sleeve defining a pouch for containing a blood pressure cuff. The sleeve is structured for fastening about a person's arm. Another type of protective sleeve for a sphygmomanometer cuff is also known that is formed as an elongated flexible envelope for receiving a blood pressure cuff. A splashproof, adjustable limb sleeve is also known that can be placed over a limb of a person. The sleeve is made from a material that absorbs moisture from the person's skin, and repels moisture from the outside. The sleeve includes an adjustable silicone seal that is sewn to each end of the protective sleeve to provide a splashproof closure between the limb and the sleeve. The sleeve is fastened around the limb by a hook and loop fastener.

It would be desirable to provide a protective liner that can be placed around the upper arm of a person and used multiple times with the individual person with a common blood pressure cuff, to protect the skin of the person, to wick moisture away from the person's skin to help prevent degradation of the person's skin, and to provide a moisture permeable, microporous microbial barrier to substantially prevent cross-contamination from repeated use of the blood pressure cuff with a number of persons.

A potential problem with liners and sleeves for use with blood pressure cuffs, particularly liners or sleeves having a thick absorbent layer, is possible interference by such liners or sleeves with detection of a person's systolic and diastolic blood pressure readings. However, recent studies have shown that differences in mean blood pressure readings taken with a cuff placed over a subject's shirt sleeve and taken over a subject's unclothed, bare arm were not significant, and were not clinically important, so that it is possible for an appropriate liner or sleeve of comparable thickness to a shirt sleeve to be suitable for use with a blood pressure cuff. It would be desirable to provide a protective liner for use with a blood pressure cuff that permits detection of a person's pulse through the protective liner, substantially without interference with measurement of the person's blood pressure. The present invention addresses these and other needs.

SUMMARY OF THE INVENTION

Briefly, and in general terms, the present invention provides for a protective liner for use with a blood pressure measuring cuff, wherein the protective liner includes multiple layers of material configured to protect the skin of the person, wick moisture away from the person's skin, and provide a moisture permeable, microporous microbial barrier. The protective liner is porous and sufficiently thin so that the protective liner will not substantially interfere with detection of a person's pulse through the protective liner and a blood pressure cuff. The multiple layers of material are configured to permit passage of water vapor therethrough while substantially preventing passage of microbes therethrough.

Accordingly, the present invention provides for a protective liner for use with a blood pressure measuring cuff on a person's arm, the protective liner being formed of a plurality of layers of material, including a first layer of material formed of woven fabric, and a second layer of material joined to the first layer of material and formed of a porous polymeric film having pores therethrough configured to permit passage of water vapor therethrough while substantially preventing passage of microbes therethrough. In a presently preferred aspect, the first layer of material is formed of a woven fabric selected from the group consisting of natural woven fabrics and synthetic woven fabrics, and is preferably formed of silk.

In another presently preferred aspect, the porous polymeric film can be a microporous film such as a polyolefin, thermoplastic elastomer, thermoset elastomer, polyurethane, poly-